US010747412B2

(12) United States Patent
Keil et al.

(10) Patent No.: US 10,747,412 B2
(45) Date of Patent: Aug. 18, 2020

(54) METHOD AND APPARATUS FOR ADJUSTMENT OF A TABLE POSITION IN A MEDICAL DATA ACQUISITION SCANNER

(71) Applicant: Siemens Aktiengesellschaft, Munich (DE)

(72) Inventors: Miriam Keil, Erlangen-Dechsendorf (DE); Christof Krellmann, Erlangen (DE); Peter Schmitt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 1189 days.

(21) Appl. No.: 15/074,337

(22) Filed: Mar. 18, 2016

(65) Prior Publication Data

US 2016/0274782 A1 Sep. 22, 2016

(30) Foreign Application Priority Data

Mar. 19, 2015 (DE) .................... 10 2015 205 004

(51) Int. Cl.
*G06F 3/0484* (2013.01)
*A61B 5/055* (2006.01)
(Continued)

(52) U.S. Cl.
CPC ........ *G06F 3/04847* (2013.01); *A61B 5/0555* (2013.01); *A61B 5/704* (2013.01);
(Continued)

(58) Field of Classification Search
CPC ....... A61B 6/583; A61B 6/032; A61B 6/4035; A61B 6/4241; A61N 2005/1087
See application file for complete search history.

(56) References Cited

U.S. PATENT DOCUMENTS

2004/0162457 A1* 8/2004 Maggiore ................ A61N 5/10
600/1
2005/0074085 A1 4/2005 Hsieh et al.
(Continued)

FOREIGN PATENT DOCUMENTS

| CN | 103815925 A | 5/2014 |
| CN | 104161533 A | 11/2014 |
| CN | 104337539 A | 2/2015 |

*Primary Examiner* — Baisakhi Roy
(74) *Attorney, Agent, or Firm* — Schiff Hardin LLP

(57) ABSTRACT

In a method and apparatus for adjusting a table position in a medical data acquisition scanner, image data relating to a body region are generated by operation of the medical data acquisition scanner by running a scanning protocol. The scanning protocol is intended to be used independently of the body region that is mapped. An iso-mode, in which a relative position of the body region relative to the isocenter of the medical data acquisition scanner can be set via the table position in accordance with an optimization criterion, and on a ref-mode, in which the table position is set at a predetermined reference position, are provided. A mode of operation is selected from the iso-mode and the ref-mode as dependent on anatomical information relating to the body region and/or a relative position of the body region relative to the isocenter that ensues in the reference position, and before the running of and/or during the running of the selected scanning protocol, the table position is set according to the selected mode of operation.

16 Claims, 6 Drawing Sheets

(51) Int. Cl.
  *G01R 33/54* (2006.01)
  *G01R 33/30* (2006.01)
  *A61B 5/00* (2006.01)
  *G06F 3/0482* (2013.01)
  *G01R 33/28* (2006.01)
(52) U.S. Cl.
  CPC ............ *A61B 5/7435* (2013.01); *G01R 33/28* (2013.01); *G06F 3/0482* (2013.01); *G06F 3/04842* (2013.01); *G01R 33/546* (2013.01)

(56) References Cited

U.S. PATENT DOCUMENTS

| | | | |
|---|---|---|---|
| 2005/0089137 A1* | 4/2005 | Toth | A61B 6/032 378/19 |
| 2005/0089138 A1* | 4/2005 | Toth | A61B 6/032 378/20 |
| 2007/0016001 A1 | 1/2007 | Graf | |
| 2007/0225588 A1* | 9/2007 | Steckner | A61B 5/0555 600/407 |
| 2008/0234531 A1* | 9/2008 | Welch | A61N 5/10 600/2 |
| 2009/0209844 A1 | 8/2009 | Gagnon et al. | |
| 2010/0040268 A1* | 2/2010 | Boeing | A61B 6/482 382/128 |
| 2011/0153231 A1* | 6/2011 | Greiser | G01R 33/56316 702/49 |
| 2012/0317724 A1 | 12/2012 | Buettner | |
| 2012/0330127 A1* | 12/2012 | Aulbach | G06F 19/321 600/407 |
| 2014/0187847 A1* | 7/2014 | Ikeda | A61N 5/1049 600/1 |
| 2014/0288410 A1 | 9/2014 | Takamori | |
| 2015/0201863 A1 | 7/2015 | Flammang et al. | |
| 2016/0228727 A1* | 8/2016 | Wachowicz | A61B 5/055 |

\* cited by examiner

METHOD AND APPARATUS FOR ADJUSTMENT OF A TABLE POSITION IN A MEDICAL DATA ACQUISITION SCANNER

BACKGROUND OF THE INVENTION

Field of the Invention

The invention concerns a method for operating a control device, in order to adjust a table position of a table relative to a medical data acquisition scanner. A body arranged on the table is intended to be examined by the medical data acquisition scanner. The invention also includes an apparatus having a medical data acquisition scanner and the control device that is operated according to the invention.

Description of the Prior Art

As used herein, an examination means the acquisition of image data for a body region of the body by operation of the medical data acquisition scanner. Such an examination or session begins with a body, for example a (human or animal) patient or a material sample of a material (for example of a metal or a rock), being placed on the table and the table then being moved into a table position or a table position being set, at which the body region that is to be examined has a favorable position relative to an isocenter of the medical data acquisition scanner. The term isocenter denotes the spatial region with the highest-quality imaging results or imaging accuracy of the medical data acquisition scanner. The isocenter can therefore be, for example, the center of the calibrated spatial region of the medical data acquisition scanner. After the desired image data relating to the body region, and in some cases relating to further body regions, has been acquired, the body may be removed from the table again. For example, the patient may leave the table, and the examination is thus completed.

The examination may be directed or monitored by a user, such as a physician or an assistant (a medical technician—MTA). With regard to the body that is arranged on the table, the user may initially search for an examination program that can be selected, for example, dependent on a feature of the body that is to be examined, an illness, for example. An examination program can be subdivided into examination steps, for example. When an examination program is running, the medical data acquisition scanner control unit can, for example, prompt the user to mark a body region, for example, a patient's liver or heart, for a first examination step in what is known as a localizer image (overview image), for example, and generate image data for this body region. The user can then adjust or position a field of view or selected range of the medical data acquisition scanner in the localizer image on the desired body region, a specific organ, for example. Furthermore, the user selects a scanning protocol, by means of which the image data is to be generated. The scanning protocol is the complete set of parameters that have to be adjusted in the medical data acquisition scanner in order to generate the required image data for the body region. The user then activates the imaging, that is, the selected scanning protocol is run. As a result thereof, the image data relating to the selected or marked body region is generated. Then, in a subsequent examination step, provision can be made for the acquisition of image data relating to a different body region. When all the examination steps have been processed, the examination program has then been completed. This completes the examination. The sequence of examination steps represents a working routine or work flow for the user.

By combining all the medical data acquisition scanner parameters required for the acquisition of image data relating to a body region in a scanning protocol, it is possible to ensure that the best image quality is achieved without the user having to worry about technical details.

One disadvantage with this, however, is that for different body regions, for example, for different body regions of a human body or different organs, a specialized scanning protocol is often required since, for example, the contrast ratios in the different regions may vary to such an extent that one scanning protocol cannot be used to acquire image data in different body regions. In other words, scanning protocols are incompatible for different body regions.

SUMMARY OF THE INVENTION

The invention addresses the problem of making scanning protocols in a medical data acquisition scanner compatible for different body regions.

According to the invention, a method is provided for operating a control device to adjust a table position of the table of the medical data acquisition scanner, in order to examine a body. The method makes provision, in a manner that is essentially known, for a user selection of a scanning protocol to be received from a plurality of possible scanning protocols. Furthermore, a user input is received, by which a body region of a body arranged on the table is stipulated. Then image data relating to the body region is generated in the known manner by the medical data acquisition scanner by carrying out the selected scanning protocol.

Now, in order to make the selected scanning protocol compatible for different body regions, provision is made according to the invention such that the scanning protocol itself does not comprise an indication or a parameter for the table position or such that the table position is ignored in the scanning protocol. Instead, the table position is specified independently of the scanning protocol. The following steps are provided to this end.

Two modes of operation are provided for the medical data acquisition scanner by the control device. In an iso-mode, a relative position of the body region relative to the isocenter of the medical data acquisition scanner is set according to a predetermined optimization criterion by adjusting the table position. In other words, in the iso-mode for each image taken, that is, for each slice-shaped picture or view of the body region, the body region that is to be mapped is moved into the isocenter. As a result thereof, when a number of scanning protocols are carried out, the table therefore also carries out a plurality of table movements. The iso-mode is therefore an active mode of operation, in which adherence to or fulfillment of the optimization criterion is monitored and/or ensured prior to and/or during the running of the scanning protocol.

In a ref-mode, the table position is set at a reference position. The reference position is independent of the relative position of the body region with respect to the isocenter. In other words, the table position is set at a predetermined value. As a result thereof, the number of table movements can be reduced during the running of the scanning protocols. The ref-mode is therefore a passive mode of operation, in which the table position is set at a predetermined reference position. In particular, the relative position does not fulfill the optimization criterion. In other words, the optimization criterion is violated by the resulting relative position.

For the aforementioned reason, in the method according to the invention, after the selection of the scanning protocol, there is still no information as to which table position has to be set. In a further process step, a mode of operation is therefore selected from the iso-mode and the ref-mode. The selection is achieved depending on anatomical information about the body region. In other words, the mode of operation is selected depending on which body region, for example which organ or which body region of a human body, is to be mapped by means of the scanning protocol.

Additionally or alternatively, the selection of the mode of operation is achieved depending on a relative position, which would ensue between the body region and the isocenter if the table were to be moved into the reference position, that is, if the reference position were to be set. Prior to the running and/or during the running of the selected scanning protocol, the table position is then set in accordance with the selected mode of operation. It may consequently be the case that one and the same scanning protocol is carried out once in the iso-mode and once in the ref-mode in order to set the table position, and indeed depending on the body region that is to be mapped and/or depending on the relative position of the body region relative to the isocenter that ensues in the reference position.

The advantageous result of the invention is that a scanning protocol can be applied to different body regions and a parameter that is decisive for image quality and the number of table movements, that is, the table position, is set independently of the scanning protocol and instead is dependent on the body region examined and/or on the suitability of the reference position. If, for example, highly precise imaging is required for a body region, then the iso-mode can be set for this. If, however, it is known with respect to a body region that this can also be mapped with sufficient precision outside the isocenter, then it can be mapped instead by means of the ref-mode from the reference position of the table so that the table does not have to be moved unnecessarily.

The invention also encompasses a number of embodiments, the features of which lead to further advantages.

One embodiment relates to the source of the anatomical information about the body region. Advantageously, the anatomical information is acquired from a patient record (patient data set) and/or from the examination program set for the examination and/or from the current examination step in the examination program. As a result, there is the advantage that the anatomical information, for example the name of an organ located in the body region, can be received from a data set in the form of text information, for example. As a result, the anatomical information is often obtainable in a clear and error-free state.

Another embodiment relates to the advantageous increase in flexibility when adjusting the table position. In this development, a user can also advantageously adjust the table position manually. To this end, the development also makes provision for a fix-mode to be provided. In the fix-mode, the table position is set at a reference position predetermined by the user. The selection between the iso-mode and the ref-mode that has already been described is now carried out if the fix-mode has been deactivated. Otherwise, the table position is set according to the fix-mode before running the selected scanning protocol, that is, the reference position that was predetermined by the user is set.

Another embodiment relates to the selection of the mode of operation depending on the relative position of the body region relative to the isocenter if the reference position were to be set as the table position. According to this embodiment, it is verified that the body region fulfills a predetermined near-enough criterion relative to the isocenter if the reference position is set as the table position. In other words, a check is carried out as to whether it is sufficient to set the reference position so that the body region is near enough to the isocenter, as defined by the near-enough criterion. If the near-enough criterion has been fulfilled, the ref-mode is selected. As a result thereof, there is the advantage that the number of different table positions set or used during the examination can be reduced or minimized and yet an adequate predetermined minimum image quality of the image data is ensured here. The image quality can be guaranteed by defining the near-enough criterion. For example, a sharpness of image and/or a contrast and/or a degree of distortion can be used as the basis for image quality.

In another version of this embodiment, the near-enough criterion includes the fact that a distance between the reference position and an optimum position calculated according to the optimization criterion is lower than a predetermined first maximum value. In other words, the optimum position is initially calculated on the basis of the aforementioned optimization criterion (as in the iso-mode) and then a distance between the reference position and the optimum position is determined. If the distance is shorter than a predetermined maximum value, the near-enough criterion has been fulfilled.

Advantageously, the aforementioned first maximum value can be set as a function of the anatomical information. As a result thereof, it can be taken into account that some body regions can also be mapped at a greater distance from the isocenter but yet with a predetermined minimum image quality than may be the case with other body regions.

According to another development, the near-enough criterion includes the fact that a distance of a point in the body region or in the selection range described that is furthest away from the isocenter is shorter than a predetermined second maximum value. In other words, the respective outermost point in the body region or in the selection range that is the greatest distance from the isocenter when the table position corresponds with the reference position is determined. This outermost point is then checked to see whether the distance thereof from the isocenter is shorter than the second maximum value. This has the advantage of guaranteeing for the entire body region that all the points are mapped with a predetermined minimum quality.

The second maximum value can be set as a function of a homogeneity value for a magnetic field of the medical data acquisition scanner. In other words, a determination is carried out of the distance from the isocenter at which a predetermined minimum quality can still be achieved. This is determined or influenced by the homogeneity of the magnetic field. Advantageously, the second maximum value is adjusted in this way to the current homogeneity value or imaging performance.

Another embodiment takes it into account that the user might wish to improve the image quality in a targeted manner by selecting the iso-mode. The iso-mode is selected automatically in the event that the user receives an ignore-focus Command. This results in even greater flexibility in the use of a scanning protocol.

In another embodiment, the reference position described is copied from a previous examination. In other words, the reference position is determined on the basis of examination data for example, which was generated at least one day before, for example. This results in the advantage that the newly generated or acquired image data is compatible with the examination data from the previous examination with respect to the reference position. This is advantageous, for example, when using image-processing algorithms, that is, for example, post-processing applications that can ensure that the same table position is set for all the images or image data that is to be processed.

In another embodiment, the reference position can be set by the user. This results in the advantage that an unsuitable reference position in the medical data acquisition scanner can simply be corrected. To this end, this embodiment ensures that, as a function of a redefine-focus command from the user, the iso-mode is set and the selected scanning protocol is carried out. For example, the scanning protocol can be a localizer protocol that is essentially known in order to obtain a localizer image or sample image or a preliminary image of the body. The resulting table position, as set therefore in accordance with the optimization criterion in the iso-mode, is then established as the reference position for the further course of the examination.

There are likewise embodiments of the invention in relation to the aforementioned optimization criterion.

One such embodiment makes provision for the optimization criterion to include the fact that a geometric center of the body region or of the selection range is arranged by adjusting the table position in the isocenter. This results in the advantage that the average value of the distance for all the points in the body region from the isocenter is particularly low.

In order to take into account the mechanical options when adjusting the table position, a version of this embodiment makes provision for the optimization criterion to have an alignment tolerance, by which the optimization criterion is fulfilled even if the geometric center has a distance from the isocenter that is shorter than a predetermined tolerance value.

The invention also includes an apparatus for the examination of a body, that is, for example, of a human or animal body of a patient.

The apparatus has the table for the body to be placed on, in addition to the medical data acquisition scanner for mapping a body region of the body. Furthermore, the control device is provided to adjust the table position. The control device is designed to carry out any or all embodiments of the method according to the invention.

In the method according to the invention and in the apparatus according to the invention, it is particularly preferable if the medical data acquisition scanner is a magnetic resonance medical data acquisition scanner. Magnetic resonance medical data acquisition scanners require a user to stipulate the body region often under time pressure and only when the body is already located on the table and is waiting to be examined. With the method according to the invention and the apparatus according to the invention, the user now has particular flexibility when selecting a scanning protocol. However, on the table, the table position is optimally set depending on the anatomical information about the body region and/or with respect to a minimization of the table movements.

DESCRIPTION OF THE PREFERRED EMBODIMENTS

The exemplary embodiment described hereinafter is a preferred embodiment of the invention. In the exemplary embodiment, however, the components of the embodiment that are described each represent individual features of the invention that are to be considered independently of one another, which in each case further develop the invention independently of one another and are thus also to be seen as a component of the invention either individually or in a different combination from that shown. Furthermore, the embodiment described can also be complemented by further features of the invention that have already been described.

In the figures, elements with an identical function are each denoted by the same reference signs.

Figure 1:
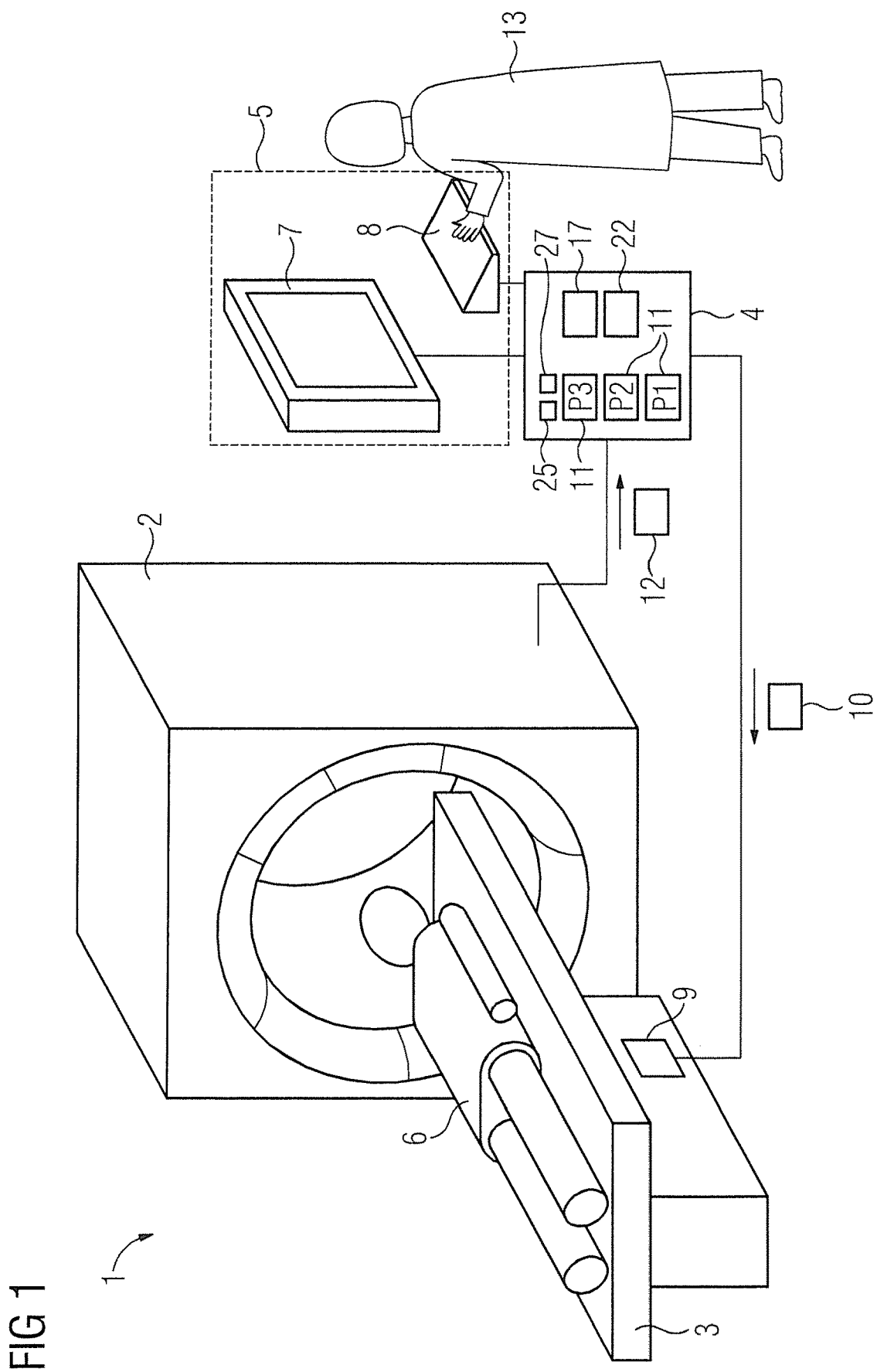
FIG. 1 schematically shows an embodiment of the apparatus according to the invention.

FIG. 1 shows an apparatus that can be installed, for example, in a hospital or a medical center or a radiology center. The apparatus 1 comprises a medical data acquisition scanner 2, a table 3, a control device 4, and optionally an operating device 5. The medical data acquisition scanner 2 can be a magnetic resonance medical data acquisition scanner, for example.

FIG. 1 shows an examination situation for an examination of a body 6, for example, of the body of a patient. Accordingly, the table 3 can be a patient table, for example. The body 6 can be arranged on the table 3. The control device 4 can be, for example, a processor or a computer. The operating device 5 can have a display device 7, a screen for example, and an input interface 8, which can include a keyboard, for example, and/or a computer mouse.

The table 3 can, in an essentially known manner, be a positioning device or adjustment device 9, by which a table position of the table 3 relative to the medical data acquisition scanner 2 can be set as a function of a control signal 10. As a result, a relative position of the body 6 relative to the medical data acquisition scanner 2 can be set or fixed, without the body itself 6 having to move. The control device 4 can be connected to the adjustment device 8, the medical data acquisition scanner 2 and the operating device 5.

By means of the control device 4, scanning protocols or short protocols 11, which are distinguished in FIG. 1 by different reference signs P1, P2, P3, can be provided. Each scanning protocol can include parameters and/or control instructions, by means of which, when it runs a protocol 11, the medical data acquisition scanner 2 generates image data 12 that shows or represent a part of the body 6. The image data 12 can be displayed, for example, by the control device 4 on the display device 7 to a user 13, who, for example, can be a physician or a technician operating the apparatus 1. The scanning protocol 11 can be selected by the user 13 via the input device 8.

In the apparatus 1, a number of table movements of the table 3 can advantageously be minimized during an examination of the body 6. It is taken into account at the same time, however, that an imaging quality of the image data 12 must have a minimum quality, however. Here, the user 13 can select a random scanning protocol 11 and apply this to any body region of the body 6, without influencing the image quality.

Figure 2:
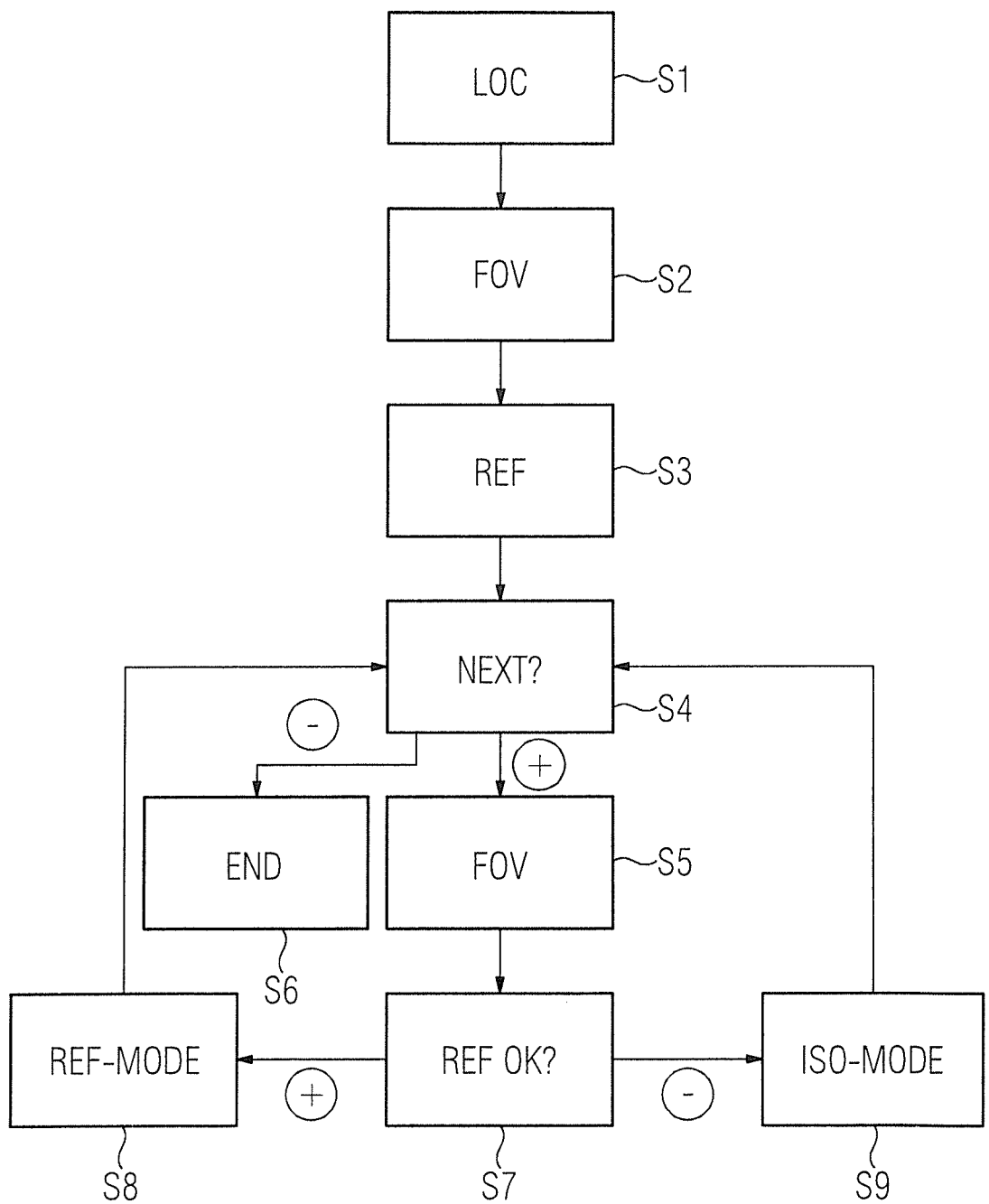
FIG. 2 is a flowchart of an embodiment of the method according to the invention, such as can be carried out by the apparatus in FIG. 1.

In order to achieve these advantages, the control device 4 can carry out the method illustrated in FIG. 2. Furthermore, reference is also made hereinafter to FIGS. 3 to 6 for an explanation of the process steps S1 to S9 that are illustrated in FIG. 2.

Each of FIGS. 3 to 6 shows a head 14 of the body 6, by way of example, illustrating how it can be mapped by means of the image data 12, for example.

Furthermore, a position of an isocenter 15, which may be located in the medical data acquisition scanner 2, is illustrated. The position of the isocenter 15 is illustrated for a table position TP, which is set by the control device 4 by means of the control signal 11 in the adjustment device 9 when the user begins, starts up, commands, or terminates the selected scanning protocol 11. Further shown is an indicator 16, which illustrates the position of the isocenter in the event that the table position TP is set at a reference position 17, the coordinates or parameters of which can be stored in the control device 4, for example. The indicator 16 is shown here by way of example as a triangle.

The positions described may, for example, each relate only to a Z-direction Z, along which the table position can be altered or set. The position information for the table positions can then be one-dimensional (a Z-value).

Figure 3:
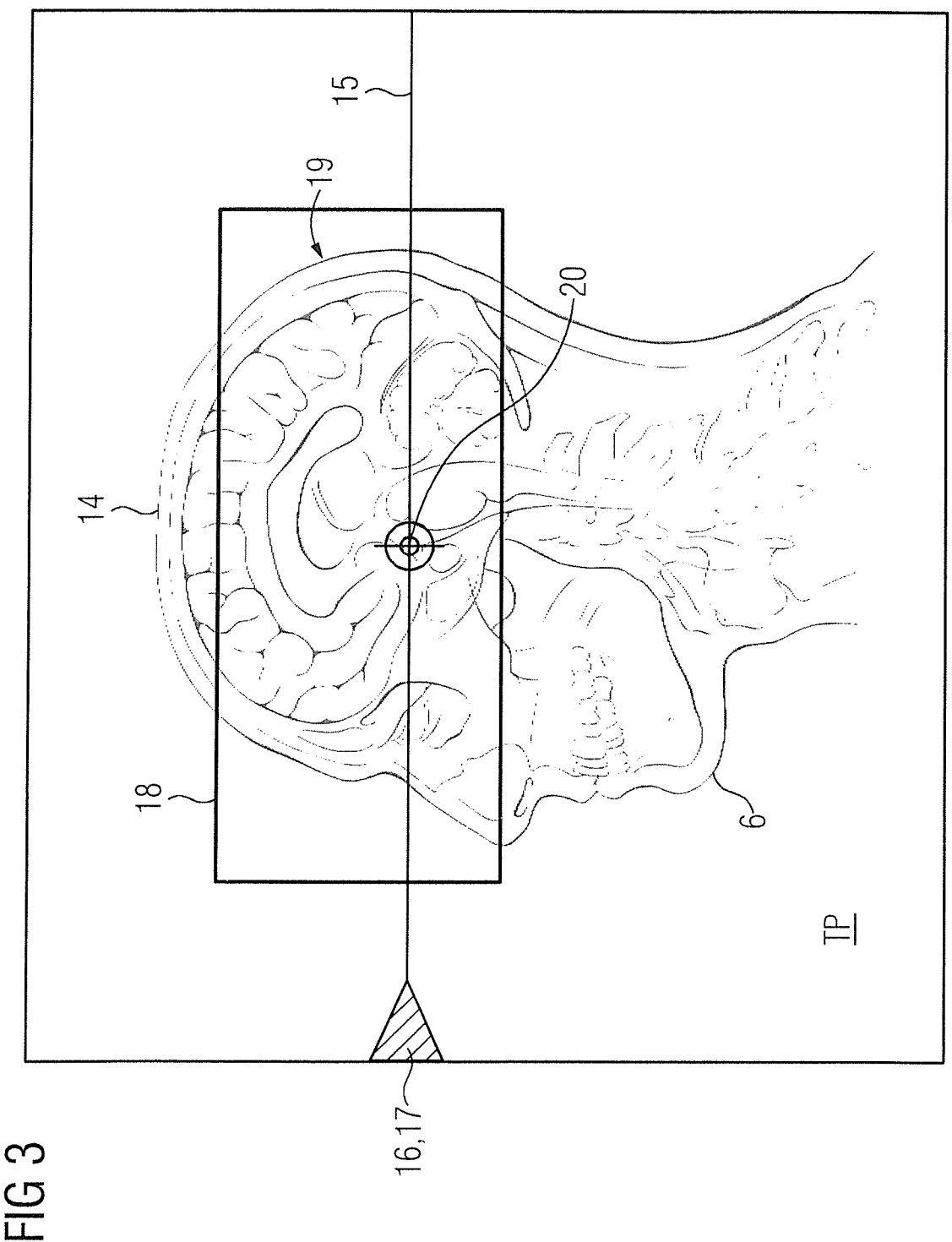
FIGS. 3 to 6 show the process steps in the method according to FIG. 2.
Figure 4:
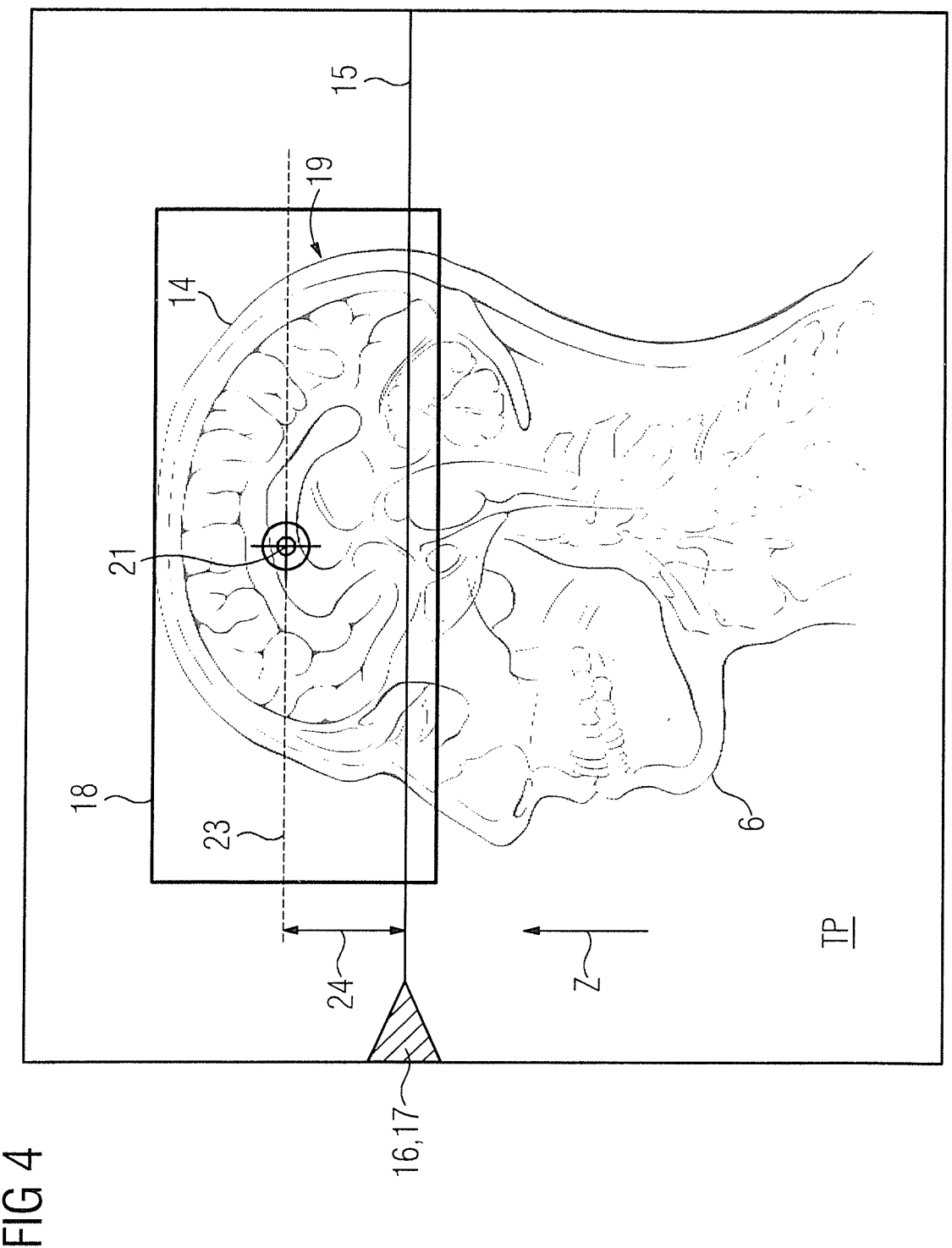

In the example illustrated in FIG. 3, the table position TP corresponds to the reference position 17, which is why the isocenter 15 and the indicator 16 are overlaid. Hereinafter, the indicator 16 is also directly denoted as the reference position 17, since it is always the position of the isocenter 15 shown by the indicator 16 that results from the reference position 17.

Furthermore, a selection region 18 is shown, the position or location of which the user 13 can adjust with respect to the body 6 by means of the input device 8. By means of the selection region 18, a body region 19 is established, the image data 12 relating to which is to be acquired by running the selected protocol 11 by operation of the medical data acquisition scanner 2.

According to the method illustrated in FIG. 2, an essentially known localizer image (LOC) can be acquired in a step S1 by means of the medical data acquisition scanner 2, which image can be displayed to the user 13 on the display device 7, for example. For example, an image which may correspond to FIGS. 3 to 6 respectively can be displayed to the user 13 on the display device 7.

In a step S2, a user 13 can set the position of the selection region 18, which corresponds with the FOV (Field of View) of the medical data acquisition scanner 2, as the part of the body to be mapped in the image data 12.

In a step S3, an optimum table position TP can be set by the control device 4 for this first adjustment of the selection region 18, for example. This position can be determined for example, in accordance with an optimization criterion according to which a geometric center 20 of the body region 19 is arranged in the isocenter 15. Then this table position TP determined by the control device 4 can be stored as the reference position 17.

In a step S4 the next examination step can then be displayed to the user 13 by the control device 4, which step the user 13 can then configure or adjust.

If the examination program that has been run results in this next examination step (symbolized in FIG. 2 by a plus sign "+"), in a subsequent step S5, the user 13 can again set a position in the selection region 18 for this examination step. If there is no next examination step (illustrated in FIG. 2 by a minus sign "−"), the examination program can be terminated in a next step S6, which terminates the examination of the body 6.

The use of the reference position 17 in the process step S5 and in the subsequent process steps S7 to S9 is explained hereinafter.

If a next examination step is to be carried out, the user can select one of the scanning protocols 11 for this. To illustrate the process step S5, it can furthermore be assumed, for example, that the user 13 will set the selection region 18 according to FIG. 4. The question now arises as to whether the isocenter 15 is now intended to be moved into the new geometric center 21. To this end, the table position TP would have to be replaced by a different table position. In other words, the table 3 would have to be moved. This would mean, however, the body 6 being given a jolt, for example. Provision can therefore be made for an alignment to be carried out between on the one hand a maximization of the image quality, by positioning the isocenter 15 in the geometric center 21 and on the other hand a reduction in the number of table movements of the table 3.

To this end, in a step S7, a near-enough criterion 22 can be provided in the control device 4 and then be verified by the control device 4. For example, according to one of the optimization criteria that have been described, an optimum position 23 can be determined and a distance 24 of the optimum position 23 from the reference position 17 can be determined. If the distance 24 does not exceed a predetermined first maximum value, that is, if the distance 24 is shorter than the first maximum value (shown in FIG. 2 by a plus sign "+"), then in a step S8, a reference mode 25 (REF-MOD) can be activated, in which provision can be made for the reference position 17 to be set on the table 3 to run the scanning protocol 11.

Figure 5:
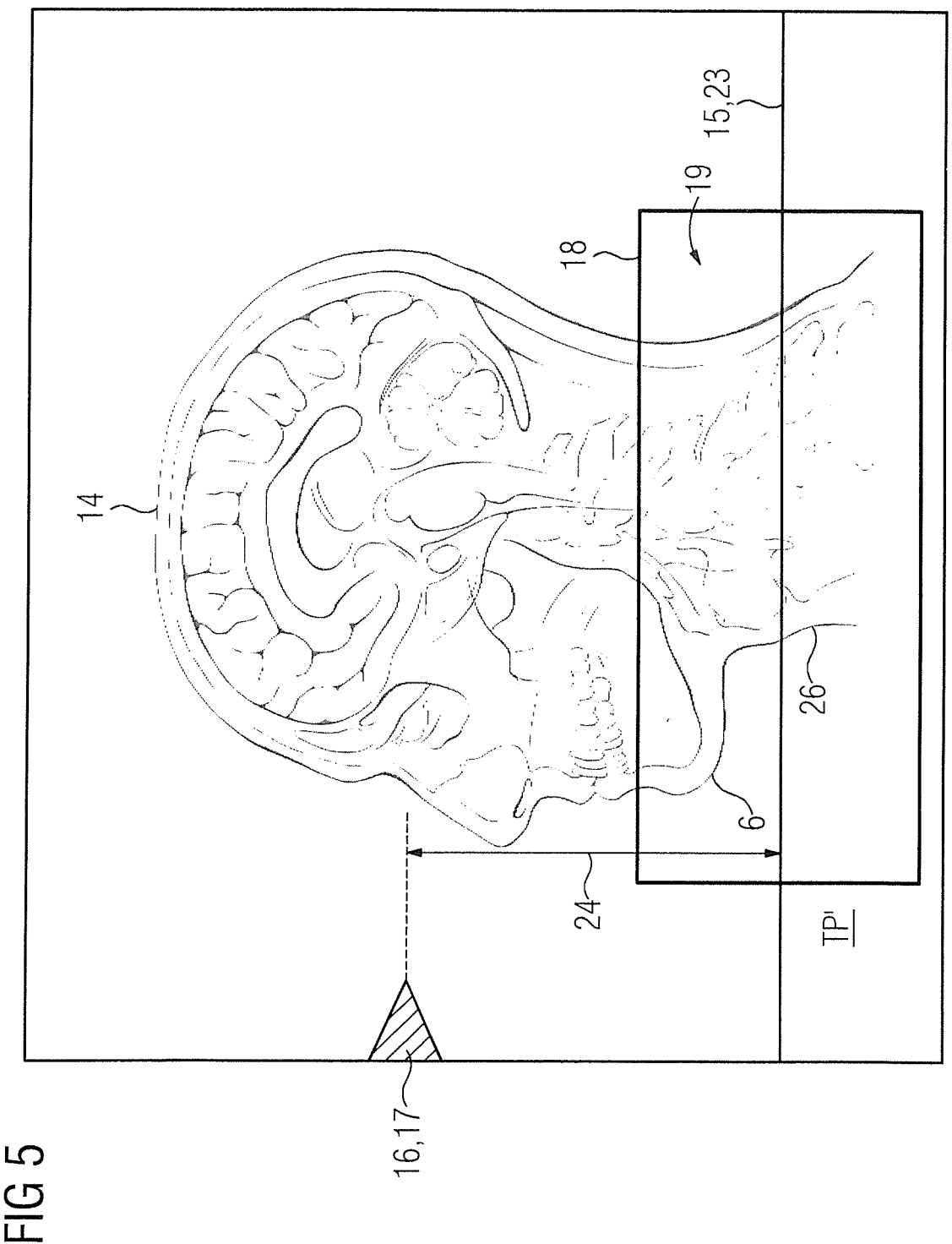

FIG. 5 illustrates a situation in which the user 13 has moved the selection region 18 and, as a result thereof, the distance 24 of the optimum position 23 is greater than the first maximum value. The user has, for example, positioned the selection region 18 in the region of a neck 26. Since the distance 24 was greater than the first maximum value, the near-enough criterion 22 was violated (represented in FIG. 2 by a minus sign "−"). In a step S9, an iso-mode 27 can be activated by the control device 4. The iso-mode 27 can make provision for the fact that a table position TP' that differs from the reference position 17 is set to run the selected scanning protocol 11. This results accordingly in a position of the isocenter 15 at the optimum position 23 for the selection region 18 that is aligned with the neck 26.

The ref-mode 25 and the iso-mode 27 each represent one mode of operation.

Figure 6:
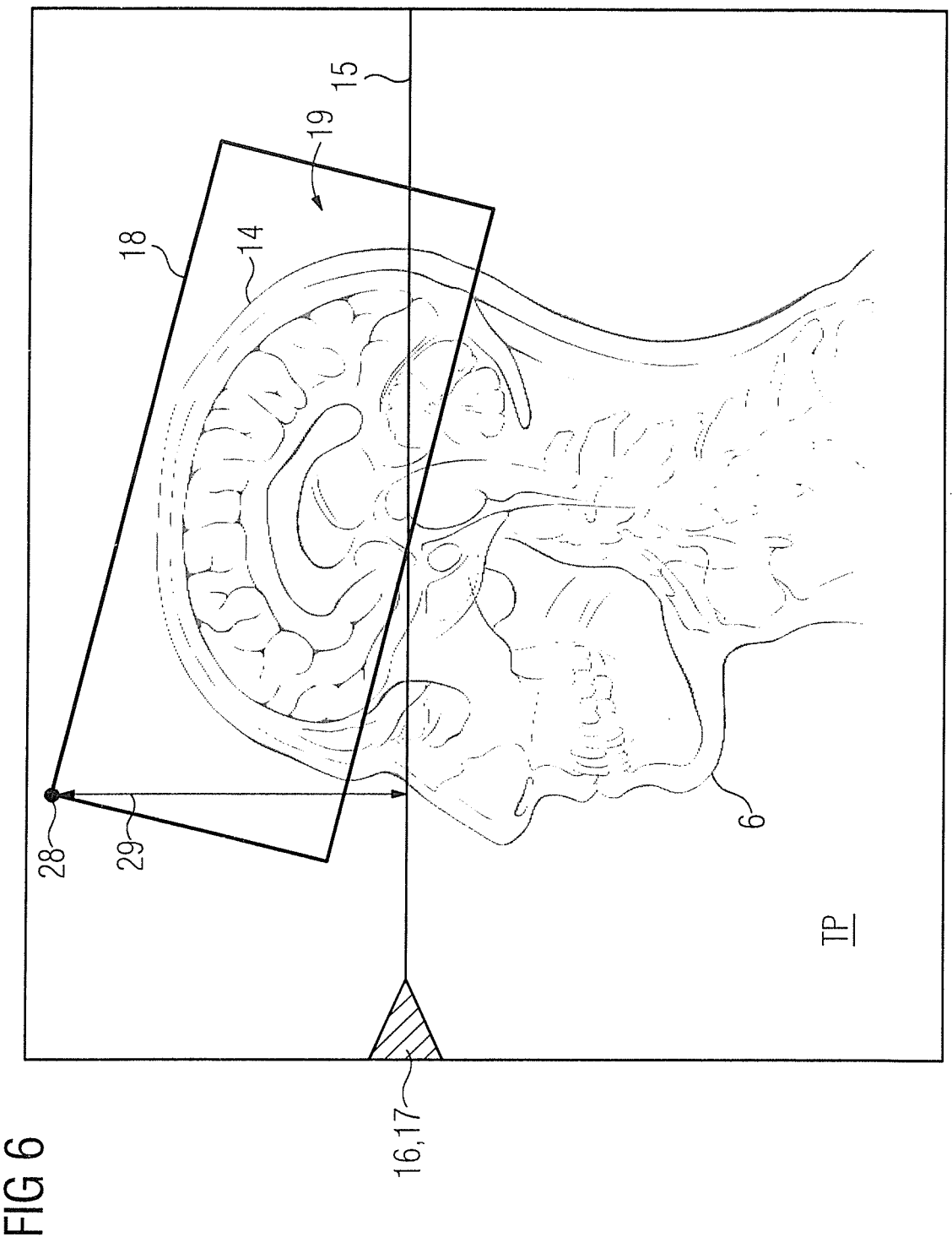

After running the selected scanning protocol 11, a further check can be carried out in step S4 as to whether a further selection step is impending. Let us assume in the example that the user 13 would like to generate an image of the head 14 again in a further examination step. FIG. 6 illustrates how, in step S5, the user 13 positions the selection region 18 at an angle, for example, in the manner illustrated in FIG. 6. In step S7, it can now be verified by the control device 4 as to whether the near-enough criterion 22 has been fulfilled. As an addition or alternative to the condition that has already been described, the near-enough criterion can, for example, include specifying that a most remote point 28 in the selection region 18 must have a distance 29 from the reference position that has to be shorter than a predetermined second maximum value so that the near-enough criterion 22 is fulfilled. The point 28 can represent the point that is furthest removed from the isocenter 15 of the body region 19 (where there is a set reference position 17). This point can also be determined directly by, for example, an image-processing algorithm, a segmentation, for example.

Let us assume in the example shown in FIG. 6 that the distance 29 is shorter than the second maximum value. Therefore, in step S8, the ref-mode 25 is set, by which the reference position 17 is set as the table position to run the scanning protocol. This results in what is known as a "snap to grid effect" or "snap to line" effect for the selection of the table position depending on the relative position of the selected body region relative to the isocenter 15 when the reference position 17 is set.

A second criterion for choosing between the ref-mode and the iso-mode may be the anatomical information about the body region 19. For example, one mode of operation can be specified for the body region "brain" and a different mode of operation for the body region "neck".

In summary, the example shows how, by operation of the invention, a body region-specific determination of the optimum table positions for MR measurements and a focus concept can be provided for the optimized planning of MR measurements.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for adjusting a table position of a patient table in a medical data acquisition scanner, wherein an examination subject is situated on the patient table, comprising:
   in a computer having a user interface, receiving an input designating a user selection of a scanning protocol, from among a plurality of scanning protocols, for operating the medical data acquisition scanner to conduct an examination of the examination subject on the patient table;
   via said user interface, receiving an input into said computer that designates a body region of the examination subject on the patient table, the body region of the examination subject being a portion of the examination subject for which the scanning protocol is to be executed via the medical data acquisition scanner;
   in said computer, generating, and presenting at said user interface, a first mode representing adjustment of the patient table position in which a relative position of the body region of the examination subject with respect to an isocenter of the medical data acquisition scanner is set dependent on an optimization criterion defining a requirement for a geometric center of said body region to be situated in said isocenter as a result of adjusting the patient table position;
   in said computer, generating, and presenting at said user interface, a second mode representing adjustment of the patient table position in which the patient table position is set at a predetermined reference position that is independent of said relative position of the body region of the examination subject with respect to the isocenter of the medical data acquisition scanner;
   via said user interface, receiving a selection input into said computer that designates either the first mode or the second mode, the selection of the first mode or the second mode being made by (i) verifying whether a distance between the body region of the examination subject and the isocenter that is determined using anatomical information of the examination subject satisfies a predetermined near-enough criterion that defines a threshold linear distance between the geometric center of the body region of the examination subject and the isocenter of the medical data acquisition scanner if the predetermined reference position were to be set as the patient table position, (ii) selecting the first mode when the near-enough criterion is not satisfied, and (iii) selecting the second mode when the near-enough criterion is satisfied;
   from said computer, emitting a control signal to said patient table that adjusts the patient table position according to the selected first mode or second mode at a time before or during execution of said selected protocol by said medical data acquisition scanner; and
   from said computer, emitting control signals to said medical data acquisition scanner that operate said medical data acquisition scanner according to the selected protocol.

2. A method as claimed in claim 1, comprising determining said anatomical information from a source including at least one of a patient record for the examination subject, an examination program forming a basis for the selected protocol, and a current examination step in said examination program.

3. A method as claimed in claim 1 comprising:
   from said computer, automatically operating said patient table and said medical data acquisition scanner by default in a third mode in which the table position is set at the predetermined reference position that is predetermined by a user entry made via said user interface; and
   permitting selection of said first mode or said second mode only if said third mode has been deactivated via said user interface, and otherwise adjusting the patient table position from said computer according to the third mode before operating the medical data acquisition scanner to execute said scanning protocol.

4. A method as claimed in claim 1, comprising employing, as said near-enough criterion, a requirement that a distance of the predetermined reference position from an optimum position that is calculated according to the optimization criterion is shorter than a predetermined maximum value.

5. A method as claimed in claim 4, comprising setting said maximum value in said computer dependent on said anatomical information.

6. A method as claimed in claim 4, wherein said maximum value is a first maximum value, and
   wherein said near-enough criterion additionally requires a distance from a point in the body region that is farthest from the isocenter to be shorter than a predetermined second maximum value.

7. A method as claimed in claim 6, wherein said medical data acquisition scanner generates a magnetic field in said medical data acquisition scanner, and comprising setting said second maximum value in said computer dependent on a homogeneity value of said magnetic field.

8. A method as claimed in claim 1, comprising allowing entry into said computer, via said user interface, of an ignore-focus command, and automatically selecting said first mode if said ignore-focus command has been entered.

9. A method as claimed in claim 1, comprising using, as said predetermined reference position, a position from a previous examination using said medical data acquisition scanner.

10. A method as claimed in claim 1, comprising setting said first mode dependent on a redefine-focus command entered into the computer via said user interface, and executing the selected scanning protocol with the patient table position set by said first mode after entry of said redefine-focus command.

11. A method as claimed in claim 1, comprising using said optimization criterion having an alignment tolerance that allows said optimization criterion to be fulfilled as long as said geometric center has a distance from said isocenter that is less than a predetermined tolerance value.

12. A method as claimed in claim 1, wherein the first mode, when selected, results in an adjustment of the patient table position such that the near-enough criterion is satisfied prior to executing the scanning protocol via the medical data acquisition scanner.

13. A method as claimed in claim 12, wherein the second mode, when selected, results in the patient table position remaining stationary and then subsequently executing the scanning protocol via the medical data acquisition scanner.

14. A method as claims in claim 1, wherein the scanning protocol is from among a plurality of scanning protocols, and
wherein the selection of the first mode or the second mode is made prior to executing each one of the plurality of scanning protocols.

15. A medical data acquisition apparatus comprising:
a medical data acquisition scanner;
a patient table adapted to receive an examination subject thereon, said patient table having a patient table position relative to the medical data acquisition scanner that is adjustable; and
a computer comprising a user interface;
said computer being configured to receive an input, via said user interface, that designates a user selection of a scanning protocol, from among a plurality of scanning protocols, for operating the medical data acquisition scanner to conduct an examination of the examination subject on the patient table, the body region of the examination subject being a portion of the examination subject for which the scanning protocol is to be executed via the medical data acquisition scanner;
said computer being configured to receive, via said user interface, an input that designates a body region of the examination subject on the patient table;
said computer being configured to generate, and present at said user interface, a first mode representing adjustment of the patient table position in which a relative position of the body region with respect to an isocenter of the medical data acquisition scanner is set dependent on an optimization criterion defining a requirement for a geometric center of said body region to be situated in said isocenter as a result of adjusting the patient table position of the body region of the examination subject with respect to the isocenter of the medical data acquisition scanner;
said computer being configured to generate, and present at said user interface, a second mode representing adjustment of the patient table position in which the patient table position is set at a predetermined reference position that is independent of said relative position of the body region of the examination subject with respect to the isocenter of the medical data acquisition scanner;
said computer being configured to receive, via said user interface, a selection input that designates either the first mode or the second mode, the selection of the first mode or the second mode being made by (i) verifying whether a distance between the body region of the examination subject and the isocenter that is determined using anatomical information of the examination subject satisfies a predetermined near-enough criterion that defines a threshold linear distance between the geometric center of the body region of the examination subject and the isocenter of the medical data acquisition scanner if the predetermined reference position were to be set as the patient table position, (ii) selecting the first mode when the near-enough criterion is not satisfied, and (iii) selecting the second mode when the near-enough criterion is satisfied;
said computer being configured to emit a control signal to said patient table that adjusts the patient table position according to the selected first mode or second mode at a time before or during execution of said selected protocol by said medical data acquisition scanner; and
said computer being configured to emit control signals to said medical data acquisition scanner that operate said medical data acquisition scanner according to the selected protocol.

16. An apparatus as claimed in claim 15, wherein said medical data acquisition scanner is a magnetic resonance tomography scanner.

* * * * *